(12) United States Patent
Keeping

(10) Patent No.: US 6,232,121 B1
(45) Date of Patent: May 15, 2001

(54) METHODS FOR THE PRODUCTION OF BIOLOGICALLY ACTIVE AGENTS CONTAINED IN AN EXTRACELLULAR MATRIX

(76) Inventor: Hugh S. Keeping, 10 King Philip Ave., Bristol, RI (US) 02809

( * ) Notice: Subject to any disclaimer, the term of this patent is extended or adjusted under 35 U.S.C. 154(b) by 3 days.

(21) Appl. No.: 09/580,109

(22) Filed: May 30, 2000

Related U.S. Application Data

(60) Provisional application No. 60/137,368, filed on Jun. 3, 1999.

(51) Int. Cl.$^7$ ........................................................ C12N 5/08

(52) U.S. Cl. .......................................... 435/402; 435/405

(58) Field of Search ...................................... 435/402, 405

(56) References Cited

U.S. PATENT DOCUMENTS 5,643,787  7/1997  Barsky et al. .

OTHER PUBLICATIONS

Ruoslahti et al, "Extracellular matrix/growth factor interactions" Cold Spring Harbor Symp. Quant. Biol. 57:30999–315 (1992).

Schultz–Cherry, S. And Murphy–Ullrich, J.E. "Thrombospondin causes activation of latent transforming growth factor–beta secreted by endolthelial cells by a novel mechanism" J. Cell Biol. 122:923–932, (1993).

Jones et al. "Extracellular matrix contains insulin–growth factor binding protein–5: potentiation of the effects of IGF–1" J. Cell Biol. 121:679–687 (1993).

Vukicevic et al "Localization of osteogenic protein–1 (bone morphogenic protein–7) during human embryonic development: high affinity binding to basement membranes" Biochem Biophys Res Comm 198:693–700 (1994).

Mereau et al "Characterization of a binding protein for leukemia inhibitory factor localized in extracellular matrix" J. Cell Biol. 122–713–719(1993).

Hanneken, A. et al. "High affinity immunoreactive FGF receptors in the extracellular matrix of vasular endothelial cells–Implications for the modulation of FGF–2" J. Cell Biol. 128:1221–1228(1995).

Lyon, M. et al. Interaction of hepatocyte growth factor with heparan sulfate, elucidation of the major heparan sulfate structural determinants: J. Biol Chem 269:11216–11223(1994).

Raines, E.W. and Ross. R. "Compartmentalization of PDGF on extracellular binding sites dependent of exon–6–encoded sequences" J. Cell Biol. 116:533–543(1992).

Park, J.E. Keller, G.A. and Ferrara, N. "The vascular endothelial growth factor (VEGF) isoforms: differential deposition into the subepithelial extracellular matrix and bioactivity of extracellular matrix–bound VEGF" Mol. Biol. Cell 4:1317–1326(1993).

Roberts, R. et al "Heparan sulphate bound growth factors: a mechanism for stromal cell mediated haemopoiesis" Nature 332:376–378(1988).

Modrowski D. et al. Glycosaminoglycans bind granulocyte–macrophage colony–stimulating factor and modulate its mitogenic activity and signaling in humanosteoblastic cells. J. Cell Physiol 177:187–195(1998).

Jones, C.A. et al, "Interleukin–4 production by human amnion epithelial cells and regulations of its activity by glycosaminoglycan binding" Biol. Reprod. 52:839–847 (1995).

Jiang, B–H et al., "V–SRC induces expression of hypoxia–inducible factor (HIF–1) and transcription of genes encoding vascular endothelial growth factor and enolase 1: Involvement of HIF–1 in tumor progression". Cancer Res. 57:5328–5335 (1997).

Benz, D.J. et al., "High affinity androgen binding and androgenic regulation of a 1(I)–procollagen and transforming growth factor–§ steady state messenger ribonucleic acid levels inhuman osteoblast–like osteosarcoma cells". Endocrinoogy 128:2723–2730 (1991).

Taiipale, J. et al., "Extracellular matrix–associated transforming growth factor–beta: role in cancer growth and invasion". Adv. Cancer Res 75:87–134 (1998).

Wu et al., "Identification of 1 alpha,25–dihydroxyvitamin D3 response elements in the human transforming growth factor beta 2 gene" Biochemistry 38:2654–2660 (1999).

Ota et al., "Nonsteriodal anti–inflammatory drugs may prevent colon cancer through supression of hepatocyte growth factor expression". Eur. J. Pharm. 367:131–138 (1999).

Gospodorwicz D. and Cheng J. "Heparin protects basic and acidic FGF from inactivation". J Cell Phys 128:475–484 (1986).

Virdi A. S., Cook L. J., Oreffo R.O.C., and Triffitt J. T. "Modulation of bone morphogenetic protein–2 and bone morphogenetic protein–4 gene expression in osteoblastic cell lines" Cell Mol Biol 44:1237–1246 (1998).

Billiau A., Edy V.G., Heremans H., Van Damme J., Desmyter J., Georgiades J.A. De Somer P. "Human interferon: Mass production in a newly established cell line, MG–63" Antimicrob Agents Chemother 12:11–15 (1997).

(List continued on next page.)

Primary Examiner—James Ketter
(74) Attorney, Agent, or Firm—Mark A. Hofer; Brown Rudnick Freed & Gesmer

(57) ABSTRACT

The present invention relates to methods for the production in vitro of cell growth supportive surfaces comprising naturally secreted human extracellular matrix material comprising biologically active agents such as growth factors ideally produced and elaborated by the extracellular matrix–secreting cells. The present invention provides an efficient method for improving growth factor potency and extending half-life in order to promote cell attachment, growth and/or differentiation. The surfaces of the present invention enable propagation of difficult cells in culture.

25 Claims, No Drawings

OTHER PUBLICATIONS

Sharp M.G., Mullins J.J., "Loss of gene function methodology" J Hypertension 11:339–343 (1993).

Kedeshina P., Sternlicht MD., Nguyen M., Shao Z–M and Barsky SH. "Humatrix a novel myoepithelial metrical gel with unique biochemical and biological properties" Cancer Letters 123:215–226 (1998).

Jones, C.A. et al., "Interleukin–4 production by human amnion epithelial cells and regulations of its activity by glycosaminoglycan binding" Biol. Reprod. 52:839–847 (1995).

METHODS FOR THE PRODUCTION OF BIOLOGICALLY ACTIVE AGENTS CONTAINED IN AN EXTRACELLULAR MATRIX

This application claims benifit of Provisional No. 60/137,368 filed Jun. 3, 1999.

INTRODUCTION

This invention relates to the production of biologically active agents in association with extracellular matrix (ECM) secreted by osteosarcoma (OS) cells generally following treatment with differentiation agents. More specifically, this invention relates to incorporation of said agents into said matrix for their efficient delivery to cells brought into contact with the matrix in vitro. Production of ECM by OS cells in vitro eliminates the need for animals in which to maintain tumors that contain ECM-producing cells. The invention also provides elimination of contamination of ECM by additional substances from other tumor cell types, which can occur in the less controlled environment of in vivo tumor growth systems.

BACKGROUND

Adhesion of cells to an extracellular matrix is mediated primarily by integrins expressed on the cell surface. Integrins are transmembrane receptors expressed on a wide variety of cells. Ligands for integrins include adhesive extracellular matrix proteins such as fibronectin, vitronectin, collagen and laminin. While purified extracellular matrix components have been used as a coating for the culturing of living cells, in purified form these components do not form the desired three dimensional matrix which characterizes extracellular matrices as they occur in vivo.

A three-dimensional basement membrane-derived extracellular composition obtained from the EHS (Engelbreth Holm-Swarm) tumor grown in mice is disclosed in U.S. Pat. No. 4,829,000. This composition when reconstituted resembles interconnected thin sheets of the lamina densa of the basement membrane to which cells attach. This same basement membrane can be provided by a continuous or immortalized mammalian cell line having the phenotypic properties of EHS murine tumor cells (U.S. Pat. No. 5,354, 666) thereby advantageously eliminating the use of mice to maintain the EHS tumor cells. However, the composition is still characterized by significant disadvantages in that it is derived from the EHS tumor, which is of mouse origin. Further, the tumor can not be manipulated to produce specific biologically active growth factors which can be vitally important to the growth, maintenance and differentiation of difficult cells.

Extracellular matrix contains proteins known to support the attachment of a wide variety of cells: fibronectin, vitronectin, thrombospondin, collagens, decorin, laminin and heparin sulfate are examples of matrix proteins. In addition to providing a scaffold for cell attachment, matrix can serve as a reservoir of ligands for growth factor receptors. A number of growth factors including insulin-like growth factor, fibroblast growth factor, members of the transforming growth factor beta family, vascular endothelial growth factor and hepatocyte growth factor have been shown to bind to extracellular matrix proteins and heparan sulfate. For example, Jones et al (J. Cell Biol 121:679–687 (1993)) describe the association of IGFBP-5 with ECM produced by human fetal dermal fibroblasts and in particular its binding to collagen Types III and IV, laminin and fibronectin as detected by polyclonal antisera assays. In addition, these growth factors may be stored in a latent form within the ECM, wherein they become activated and effect cell growth, differentiation or behavior. Still other investigators (Park et al) have shown that degradation of ECM, produced by human embryonic kidney cells grown on plastic, can release or mediate FGF growth factor activity (Mol. Bio Cell 4:1317–1326 (1993)). It is an aspect of the present invention to provide procedures for controlling the amount and type of growth factors present in ECM and not to rely on serendipitous, uncontrolled production as investigators have traditionally done and in particular to be able to control the amount and presence of FGF, BMP and IGF-1 alone and in co-mixture in ECM.

Growth factors tend to be highly unstable both in vivo and in vitro. This characteristic has hampered studies designed to elucidate their effects on cells cultured in vitro and as biological response modifiers when administered therapeutically to laboratory animals in vivo. In attempts to improve delivery in vivo, synthetic delivery systems have been prepared by incorporating active agents such as growth factors within a vehicle containing matrix material. Previous efforts are exemplified by the use of hydrophobic polymers such as ethylene vinyl acetate (Gospodorwicz et al J Cell Phys 128:475–484, 1984). Hunziker (U.S. Pat. Nos. 5,206, 023; 5,270,300; 5,368,858) disclose the use of matrix materials such as fibrinogen, collagen, Sepharose and gelatin. Other investigations have utilized collagen-binding ligand-active agent matrices for improved growth factor delivery in vivo. Vuori et al (U.S. Pat. No. 5,830,504) discloses the formation of a synthetic matrix by conjugating a biodegradable polymer to an alpha V-beta3 ligand and a growth factor receptor ligand. In these conventional approaches, the composition were prepared synthetically by mixing or incorporating the purified active agent into the vehicle with the intent of delivering such agent in vivo.

It is an aspect of the present invention to avoid the unnatural characteristics imposed by such approaches. It is another aspect of the present invention to provide for preparing complex extracellular matrices containing active agents (such as growth factors) for the cultivation of difficult cells in vitro.

While one product, Matrigel ™ offered by Becton Dickinson and Company (N.J.), purports to provide some of these advantages by providing a plate having deposited thereon ECM with growth factors incorporated, this product contains poorly characterized growth factors in terms of regulation of the type and quantity of growth factors present. As a consequence, this product is more of a research curiosity and is difficult to use in a controlled fashion.

It is yet another further aspect of the present invention to improve upon such products and to provide methods for producing ECM on surfaces having predetermined growth factors or mixtures thereof in known concentrations.

It is still another aspect to provide ECM with desired growth factors incorporated therein which will be more useful for research and production purposes than conventional approaches.

Additional understanding of the state of the art and general knowledge of the skilled artisan may be had by reference to the following, which, like the references cited elsewhere, are fully incorporated herein:

U.S. Patent Documents:
  U.S. Pat. No. 4,829,000, May, 1989, Kleinman, et al.
  U.S. Pat. No. 5,354,666, October, 1994, Danielson et al.
  U.S. Pat. No. 5,770,448June, 1998, Jones, et al Publications:

Ruoslahti et al, "Extracellular matrix/growth factor interactions" Cold Spring Harbor Symp. Quant. Biol. 57:309–315 (1992).

Schultz-Cherry, S. and Murphy-Ullrich, J. E. "Thrombospondin causes activation of latent transforming growth factor-§ secreted by endothelial cells by a novel mechanism" J. Cell Biol. 122:923–932, (1993).

Jones et al. "Extracellular matrix contains insulin-like growth factor binding protein-5: potentiation of the effects of IGF-1" J. Cell Biol. 121:679–687 (1993).

Vukicevic et al "Localization of osteogenic protein-1 (bone morphogenic protein-7) during human embryonic development: high affinity binding to basement membranes" Biochem Biophys Res Comm 198:693–700 (1994).

Mereau et al "Characterization of a binding protein for leukemia inhibitory factor localized in extracellular matrix" J. Cell Biol. 122–713–719 (1993).

Hanneken, A. et al. "High affinity immunoreactive FGF receptors in the extracellular matrix of vascular endothelial cells-Implications for the modulation of FGF-2" J. Cell Biol. 128:1221–1228 (1995)

Lyon, M. et al. "Interaction of hepatocyte growth factor with Heparan sulfate, elucidation of the major heparan sulfate structural determinants: J. Biol Chem 269:11216–11223 (1994).

Raines, E. W. and Ross, R. "Compartmentalization of PDGF on extracellular binding sites dependent of exon-6-encoded sequences" J. Cell Biol. 116:533–543 (1992).

Park, J. E., Keller, G. A. and Ferrara, N. "The vascular endothelial growth factor (VEGF) isoforms: differential deposition into the subepithelial extracellular matrix and bioactivity of extracellular matrix-bound VEGF" Mol. Biol. Cell 4:1317–1326 (1993).

Roberts, R. et al "Heparan sulphate bound growth factors: a mechanism for stromal cell mediated haemopoiesis" Nature 332–376–378 (1988).

Modrowski D et al. "Glycosaminoglycans bind granulocyte-macrophage colony-stimulating factor and modulate its mitogenic activity and signaling in humanosteoblastic cells. J. Cell Physiol 177:187–195 (1998)

Jones, C. A. et al. "Interleukin-4 production by human amnion epithelial cells and regulations of its activity by glycosaminoglycan binding" Biol. Reprod. 52–839–847 (1995).

Jiang, B-H et al., "V-SRC induces expression of hypoxia-inducible factor (HIF-1) and transcription of genes encoding vascular endothelial growth factor and enolase 1: Involvement of HIF-1 in tumor progression". Cancer Res. 57:5328–5335 (1997).

Benz, D. J. et al. "High affinity androgen binding and androgenic regulation of a1(I)-procollagen and transforming growth factor-§ steady state messenger ribonucleic acid levels inhuman osteoblast-like osteosarcoma cells". Endocrinology 128:2723–2730 (1991).

Taipale, J et al. "Extracellular matrix-associated transforming growth factor-beta: role in cancer growth and invasion". Adv. Cancer Res. 75:87–134 (1998).

Wu et al. "Identification of 1 alpha, 25-dihydroxyvitamin D3 response elements in the human transforming growth factor beta 2 gene" Biochemistry 38:2654–2660 (1999).

Ota et al. "Nonsteriodal anti-inflammatory drugs may prevent colon cancer through suppression of hepatocyte growth factor expression" Eur. J. Pharm. 367:131–138 (1999).

BRIEF SUMMARY

In accordance with the present invention, methods of coating tissue culture plasticware with a naturally secreted three-dimensional extracellular matrix containing ligands for one or more growth factor receptors and the resultant cell growth supporting devices are disclosed. These methods advantageously permit the manipulation of the parameters involved in growth factor production and secretion to permit the production of ECM comprising controlled amounts or levels of one or more growth factors.

In contrast to prior approaches, the methods of the present invention provide a complex extracellular matrix containing at least one but most preferably multiple growth factors which are also secreted by the cells which secrete the matrix. Such an extracellular matrix can surprisingly and advantageously modulate cellular attachment, growth and differentiation by serving as a reservoir for growth factors and by decreasing their rate of degradation, thus pro-longing their in vitro half-life. The methods advantageously also permit the production of ECM coated plates or other cell growth support surfaces which are largely identical in terms of the types of cell growth factors contained but which differ based on the relative concentrations thereof.

The devices of the present invention also enhance cell growth and attachment by providing a naturally secreted extracellular matrix to promote cell attachment along with ligands for growth factor receptors contained within the matrix. This composition can ideally be used to enable the growth and maintenance of cells, which are either very difficult or impossible to adequately grow in vitro.

The present invention takes advantage of the unexpected findings that: (1) osteosarcoma cell lines can be manipulated by various differentiating agents to alter the production of ligands for growth factor receptors, (2) ligands for growth factor receptors bind to components of the extracellular matrix by said cells resulting in prolonged half life and increased potency of the growth factor and, (3) cell growth is enhanced in a synergistic manner when cells bind to growth factor receptor ligands in combination with ligands to integrins.

DETAILED DESCRIPTION AND BEST MODE

The term "ligand" to a growth factor receptor as used herein refers to all compounds capable of binding to one or more cellular receptors thereby activating cells containing such receptors. Binding and activation can be conveniently determined by well known receptor-ligand binding techniques and cell-based assays, which are known to those skilled in the art.

The terms "cell line" and "established cell line" are used herein in conformance with the definitions published by Federoff in the Tissue Culture Association Manual, Vol. 1, No. 1, pp. 53–57 (1975). For purposes of this invention, by the term "established" cell line is meant to mean a cell line which demonstrates the potential to be subcultured indefinitely in vitro. This is in accordance with the proposed usage of animal tissue culture terms by S. Federoff accepted by the Tissue Culture Association at its Annual Meeting on Jun. 3, 1966 in San Francisco.

Cell growth factors, such as granulocyte-macrophage colony stimulating factor (GM-CSF), bone morphogenic proteins (BMP), and interleukins (IL) primarily affect cell proliferation and differentiation. However, many of these growth factors are unstable and break down during incubation periods when they are brought into contact with cells. The methods of the present invention provide an in vitro system to stabilize such growth factors patterned in part on the observation that in vivo growth factors can be found bound to specific components of the extracellular matrix in bodily tissues.

Growth factor receptor ligands include those secreted by cells also secreting extracellular matrix, as well as substantially purified growth factors in all active forms, or biologically active analogs thereof. These growth factor receptor ligands may be obtained by synthetic, recombinant techniques, or from commercial sources, as would be known by someone skilled in the art. Growth factor receptor ligands may also be obtained from sources other than the cells secreting the extracellular matrix and in such instances would then need to be added to the secreted matrix under conditions in which binding to components of the matrix would occur.

Mammalian genes are typically regulated in an inducible, cell type-specific or constitutive manner. There are various structural aspects of genes, which control its regulation. For example, DNA binding proteins or transcription factors recognize specific sequences within a gene (called cis-acting elements). The binding of these DNA binding proteins to the gene is responsible for the initiation, maintenance, or down-regulation of its expression. Useful guidance for this approach can be had by reference to Ausubel F M, et al. DNA-protein interactions, Chp 12. in Current Protocols in Molecular Biology, Greene Publishing Associates, Inc. and John Wiley & Sons, Inc. 1993.

The cis-acting elements which control genes are called promoters, enhancers or silencers. Promoters are positioned next to the start site of transcription and function in an orientation-dependent manner, while enhancer and silencer elements, which modulate the activity of promoters, are flexible with respect to their orientation and distance from the start site of transcription. There are various types of inducible elements including hormone-responsive elements, glucocorticoid-responsive elements, metal-responsive elements (MREs), heat shock-responsive elements, hypoxic-responsive elements, interferon-responsive elements and cytokine-responsive elements. Preferred embodiments of the present invention advantageously utilize such known elements within the ECM-producing cell to enable modulation of cellular based genetic processes to alter the production and secretion of various growth factors which in turn will be incorporated into the extracellular matrix.

Extracellular signals modulate the activity of many types of transcription factors. One important group of signal-regulated transcription factors comprise the BZip proteins, named because of their conserved basic (B) and leucine zipper (Zip) domains that are required for DNA binding and dimerization, respectively. Some well-studied examples of this family of transcription activator proteins include the AP-1/jun/fos family of transcription factors and the CREB/ATF proteins which bind to the TPA (12-O-tetradecanoylphorbol-13-acetate) response element and cyclic AMP (cAMP) response element (CRE), respectively. Regulation by BZip proteins can involve a variety of complex mechanisms-transcriptional, temporal and post-translational-that affect the level and the repertoire of the factors expressed in a given cell, as well as their DNA binding and transcriptional activation functions. The present invention also advantageously enables the use of BZip proteins in a biologically active fashion.

The production and secretion of growth factors by matrix-secreting cells can be advantageously regulated by contacting the growth hormone secreting cells with effective amounts of a variety of agents including steroids, hormones, cytokines, biological response modifiers, chemicals as well as by regulating culture conditions. Treatment of such matrix secreting cells with such factors can result in either the increased or decreased production of growth factors. For example, MG63 osteosarcoma cells normally produce bone morphogenic protein-2, which can be completely suppressed by treatment with either retinoic acid or interleukin-6 (Virdi et al Cell Mol Biol 44:1237, 1998). TE85 cells, which advantageously produce little or no IGF-2 (known to cause cells to multiply), increase production of transforming growth factor-beta when cultured with androgens or estrogens (Benz et al Endocrinology 128:2723, 1991). Exposure of a variety of normal and tumor cells to either hypoxia (1% oxygen) or chemical mimics of hypoxia (cobalt chloride or dexferrosamine) increase secretion of vascular endothelial growth factor (Jiang et al. Can Res 57:5328, 1997). In certain circumstances, production or inhibition of specific gene products can also be achieved by genetic engineering of matrix-secreting cells. Ideally, the use of regulatable promoters (e.g., tetracycline, metallothionein sensitive promoters) lends an increased aspect of control regarding the amount of growth factor produced. Preferably, these factors or treatments will be applied to matrix-producing cells during the elaboration of the extracellular matrix to the increase or decrease secretion of interesting or desired growth factor(s) into the matrix as desired. In such instances, the duration of the treatment will correlate strongly with the amount of growth factor produced or diminished relative to constitutive levels. In preferred embodiments of the present invention, a portion of elaborated growth factor will remain bound to components of the matrix following removal of the living, matrix secreting cells. The surprising result is a naturally secreted extracellular matrix with selfcontained quantifiable levels of growth factors that can facilitate and enable the attachment and growth of difficult cells, which are desired to be cultured.

EXAMPLE 1

Growth Factor Considerations

Specific examples of growth factors which have been discovered to bind extracellular matrix components and retain effective biological activity include: TGF-β binding to decorin, fibronectin, collagen type IV (Ruoslahti et al Cold Spring Harbor Symp. Quant. Biol. 57:309 (1992)), and thrombospondin (Schultz-Cherry and Murphy-Ullrich J. Cell Biol. 122:923 (1993)); insulin-like growth factor binding to insulin-like growth factor binding protein-5 (Jones et al J. Cell Biol 121:679 (1993)); BMP-2,-7 binding to collagen type IV (Vukicevic et al Biochem Biophys Res. Comm. 198:693 (1994)); LIF binding to a 160 kDa matrix protein (Mereau et al J. Cell Biol. 122:713 (1993); and fibroblast growth factor binding to matrix fibroblast growth factor receptors (Hanneken et al J. Cell Biol. 128:1221 (1995)).

The largest group of growth factor extracellular matrix (ECM) interactions have been attributed to binding to heparan sulfate proteoglycans. Examples of growth factors known to bind to heparan sulfate include hepatocyte growth factor (Lyon et al J.Biol Chem 269:11216 (1994)), vascular endothelial growth factor (Park et al Mol. Biol Cell 4:1317 (1993), platelet-derived growth factor (Raines and Ross J. Cell Biol. 116:533 (1992)), granulocyte-macrophage colony stimulating factor (Roberts et al Nature 332:376 (1988) and interleukin-4 (Jones et al Biol. Reprod. 52:839 (1995).

EXAMPLE 2

Production of ECM with TGF-β

A specific example of the regulation of growth factor production by cells secreting extracellular matrix involves secretion of TGF-β. Transforming growth factor-beta secretion and synthesis can be significantly increased by treating matrix-secreting cells with 1,25(OH)dihydroxyvitamin D3 (Wu et al. Biochem 38:2654 (1999)). TGF-β is secreted in active and latent forms which then bind to extracellular matrix components where the TGF-β is activated by cells growing on the matrix (Taipale et al Adv Can Res 75:87 (1998)).

EXAMPLE 3

Controlling Production of Growth Factors

Production and synthesis of hepatocyte growth factor may also be advantageously accomplished by stimulation of cAMP with effective amounts of prostaglandins, cholera toxin and 8-bromo cAMP (Ota et al Eur J Pharm 367:131 (1999)). Hepatocyte growth factor then binds to heparan sulfate proteoglycans and is advantageously retained in the matrix where it can advantageously affect the growth of subsequently applied cell cultures.

EXAMPLE 4

Production of ECM with Growth Factors

In alternative embodiments of the present invention, the production of a natural extracellular matrix is achieved in vitro and contains defined growth factors at ascertainable and reproducible concentrations. Matrix-producing cells are ideally cultured on the desired surface material such as plastic plates under conditions favorable for ECM deposition, such as after plating at high cell plating density and the achievement of confluency. The cells are ideally maintained in culture until sufficient deposition has occurred, usually 3–7 days after the cells become confluent. An especially useful matrix-producing cell line is the established cell line, MG-63. The MG-63 cell line was derived from an osteosarcoma by A. Billiau as reported by Billiau et al.(Antimicrob. Agents Chemother. 12 (1), 11–15 (1977)). Cultures of this cell line may be obtained directly from A. Billiau, Rega Institute for Medical Research, Leuven, Belgium, and from the American Type Culture Collection, Rockville, Md., under the code designation ATCC CRL 1427.

After production of the matrix, the matrix-producing cells are killed and may be advantageously removed by a number of well-known methods. For example, the matrix-producing cells can be killed by quick freezing using liquid nitrogen in the absence of a cryopreservative. Thereafter the cells are lysed hypotonically with distilled water. Removal is accomplished by treatment with EDTA or by enzymatic methods which allow for separation of the cellular membrane from the extracellular matrix. Alternatively, the cells can be lysed with nonionic solubilizing agents such as TRITON X-100, NonIdetP-40, CHAPS, TWEEN 20, BRIJ-35 or by ionic detergents such as SDS. Following dissolution of the matrix-producing cells, the matrix is ideally cleansed of the potentially contaminating cellular contents and debris by aspiration and washing. The contamination here occurs in the sense of creating an unknown or uncontrolled environment filled with varying levels of undefined proteins from the matrix-producing cells, the effect of which on subsequent cell growth is unknown and unpredictable and can thus diminish the use of the resultant cell growth device in sensitive assays or other experimental research uses. The extracellular matrix is ideally then sterilized using noxious gas such as ethylene glycol or by gamma radiation in doses set minimally at 20M rads to destroy any bacteria, fungi or viruses which might be present as additional contaminating elements. Cell culture plates prepared in this manner may then be used to enable the culture of difficult cells such as endothelial, neuronal, hepatocyte, mesenchymal, stem or smooth muscle cells.

ECM-producing cells cultured on devices of the present invention exhibit at confluency a saturation density of about $1\times104$ cells/cm2 to $1\times105$ cells/cm$^2$. Multilayering is not seen. At saturation density cells became rounded and refractile.

The ECM-producing cell lines may also be maintained in serum-free medium containing insulin, transferrin, and selenium (ITS). The skilled artisan will appreciate that use of serum-free, chemically-defined media facilitates the experimental manipulation of expression of endogenous growth factor genes by the ECM-producing cells and also prevents contamination of the ECM by serum components after lysis of the cells.

EXAMPLE 5

Surfaces

The substrate used herein may be selected from amongst a number of desirable substrates comprising plastic, glass or metal in flat or otherwise shaped forms. Coating of shaped articles may include forms such as sheets, fabrics, prostheses, metals and implantable articles. For example, prostheses such as artificial balls for ball joint replacements have historically been cemented in place by placing the end distal to the ball within the hollowed end of the femur and securing it in place with a potting/adhesive compound. While this approach works well in most instances, with brittle bones, previously traumatized sites or elderly patients, problems often arise in adequately immobilizing such prostheses in place. In all cases, use overtime weakens the attachment often leading to a repeat surgery. The present invention provides an alternative approach to immobilization efforts by creating a surface, which supports the growth of osteoclasts and other bone forming cells thereby providing development of a natural biological attachment. Over time, this "living attachment" may prove more durable than methods presently employed and more tolerated in challenged sites.

EXAMPLE 6

Increased Growth Factor Production by Gene Manipulation Using

Biomimetric PeptidesSpecific growth factor gene production may be up-regulated by treatment of the ECM-producing osteosarcoma cell line with a biomimetric peptide. In this embodiment of the present invention, the biomimetric peptide activates a cell surface receptor on the osteosarcoma cells which activates a signaling cascade leading to increased gene transcription of a particular growth factor. By utilizing this method, the ECM producing osteosarcoma on other cells may be altered to increase the deposition of growth factor bound to the ECM after such cells are lysed and advantageously removed from a particular surface using methods previously described.

EXAMPLE 7

Antisense Growth Factor Down-Regulation

Production of a particular growth factor may be down-regulated by treating a ECM-producing osteosarcoma or other cell line with a specific antisense RNA sequence to that growth factor in question. This treatment will prevent the expression of messenger RNA for that specific growth factor and subsequently greatly decrease or even prevent its production. This method will result in the selective down-regulation of a specific growth factor without altering the production and secretion of other growth factors. In this way, the ECM producing cells may be manipulated to produce single or multiple growth factors bound to the ECM after such cells are advantageously removed using methods previously described. Additional useful guidance may be had in employing antisense techniques by reference to Sharp, M. G., Mullins, J. J., Loss Of Gene Function Methodology, J. Hypertension 11:339–343 (1993).

EXAMPLE 8

Application to Cell Based Therapies

The growth factor/ECM compositions described in the present invention may be advantageously utilized for the propagation of cells to be used for transplantation or other type of cell based therapy for patients. In this example, such cells may be either autologous or allogeneic in nature and are chosen based on availability, convenience or as circumstances dictate. The cultivation of such cells on the growth factor/ECM coated cultureware of the present invention may allow for a stabile environment, reproducible exposure to growth factors, as well as a decreased rate of cell death. These advantages could translate into faster and/or more robust production of such transplantation cells which would in turn permit earlier treatment of the patient, especially critical in life threatening situations such as those encountered by burn patients.

EXAMPLE 9

Growth Environments for Stem Cells

The growth factor/ECM compositions described in the present invention may also be used for the cultivation and propagation of pluripotent stem cells. Such cells are usually very difficult to grow in vitro and often require feeder layers of cells and/or multiple combinations of growth and differentiation factors present in the culture media. As an alternative to these time consuming, skill dependent and expensive techniques, the embodiments of the present invention could facilitate the creation of a cell growth environment that is favorable for the maintenance of stem cells and possibly also their growth without differentiation.

EXAMPLE 10

Use in Testing Gene Products on Cells

Plastic plates coated with growth factor/ECM compositions described in the present invention may be advantageously used to support cell populations in turn used for high throughput screening of potential therapeutically active agents by assaying for cell changes following application thereof or for detecting the production of various gene products characteristic of cells, cell growth phase, or therapeutic treatment. To accomplish this, individual wells of 96 or 384 well plates are coated with ECM comprising one or multiple growth factors produced by the methods of the present invention. These coated multiwell plates are then seeded with the particular cell which forms the basis of the assay for the effect to be detected. The use of the ECM with growth factor(s) more closely simulates the natural cellular environment and thus results in a more accurate determination which could lead to improved compound selection and prediction of in vivo effects.

EXAMPLE 11

Production of Growth Factor with Accessory Cell Lines

While the most preferred embodiments of the present invention involve the manipulation of the ECM producing cell line in order to produce ECM with the desired growth factors present, both in terms of identity and concentration, there may be occasion when economics or other factors dictate the employment of an ECM producing cell line that does not produce any or negligible amounts of growth factors. In such instances, the ECM secreting cell line will be employed to produce and deposit the ECM on the desired surface following which the cells are removed. Thereafter, a second cell line or multiple cell lines as needed, are grown on the ECM under conditions which promote the cell line(s)' production and secretion of the desired growth factors into the ECM. Such cells may themselves be genetically modified or chemically treated or environmentally challenged so that the production of the desired growth factors is promoted. Following the deposition of the growth factors onto and/or into the ECM, such cells are then also advantageously removed using methods previously described. While the process has been described in terms of a sequential culture of the ECM and then the growth factor producing cells, it is also contemplated that the cells could be co-cultured. In particular, co-culture could result in improved incorporation of the growth factor within the ECM and of course, would reduce the number of physical cell removal steps required.

It will be readily appreciated by those skilled in the art after reading the present disclosure that numerous additional variations and examples can be made without departing from either the spirit or scope of the invention and that all such further examples are included within the scope of the appended claims.

What is claimed is:

1. A method for producing a surface for supporting the growth, attachment and/or differentiation of cells comprising the steps of:
   providing osteosarcoma cells;
   growing the osteosarcoma cells on a surface under conditions that promote the secretion by the cells of an extracellular matrix comprising at least one biologically active growth factor, wherein the extracellular matrix and the growth factor are concomitantly produced and said extracellular matrix is attached to said surface; and
   separating the osteosarcoma cells from the matrix, while leaving the matrix substantially intact.

2. The method of claim 1 wherein the osteosarcoma cells are selected from the group of osteosarcoma cell lines including TE85, SaOS-2, MG-63 and U-2.

3. The method of claim 2, wherein the osteosarcoma cells are TE85 cells.

4. The method of claim 2, wherein the osteosarcoma cells are SaOS cells.

5. The method of claim 1 further comprising the step selected from contacting the osteosarcoma cells with an agent or exposing the cells to culture conditions to alter production by the osteosarcoma cell of said at least one growth factor.

6. The method of claim 5 wherein the agent comprises a glucocorticoid.

7. The method of claim 6 wherein said glucocorticoid is selected from dexamethasone, cortisone and hydrocortisone.

8. The method of claim 5 wherein the agent elevates intracellular cAMP.

9. The method of claim 8 wherein the agent is selected from prostaglandin E2, 8-bromo-cAMP and cholera toxin.

10. The method of claim 5 wherein the agent reduces intracellular cAMP.

11. The method of claim 5 wherein the osteosarcoma cells are exposed to conditions of hypoxia or a hypoxia mimicking agent.

12. The method of claim 11 wherein the hypoxia mimicking agent is selected from cobalt chloride and dexferrosamine.

13. The method of claim 1 further comprising the step of exposing the osteosarcoma cells to regulation factors selected from retinoic acid, phorbol ester (12-O-tetradecanoylphorbol 13-acetate; TPA) and 1,25(OH)2 vitamin D3.

14. The method of claim 1 further comprising the step of exposing the osteosarcoma cells to estrogens or androgens.

15. The method of claim 1 wherein the separating step comprises dissolving the osteosarcoma cells in Triton X-100.

16. The method of claim 1 further comprising the step of exposing the osteosarcoma cells to agent means for altering growth factor production.

17. A method for growing mesenchymal, epithelial or stem cells comprising the steps of:

providing the cell growth surface produced by the method of claim 1;

contacting said surface with said mesenchymal, epithelial or stem cells;

providing said mesenchymal, epithelial or stem cells with cell growth under conditions for supporting cell growth and allowing said cells to grow.

18. The method of claim 17 wherein said mesenchymal, epithelial or stem cells are mammalian cells.

19. The method of claim 18 wherein said mammalian cells are human cells.

20. The method of claim 17 wherein said mesenchymal, epithelial or stem cells are plant cells.

21. The method of claim 17 wherein said mesenchymal, epithelial or stem cells are fish cells.

22. The method of claim 17 wherein said mesenchymal, epithelial or stem cells are insect cells.

23. The method of claim 1 in which the osteosarcoma cell does not secrete a growth factor with the matrix but instead, following removal of the osteosarcoma cells, at least one substantially pure growth factor or a biologically active analog thereof is added to the secreted matrix under conditions which permit binding of the growth factor to matrix.

24. The method of claim 23 wherein the growth factor is added by culturing the matrix with at least one cell line different than the matrix producing osteosarcoma cell line under conditions wherein said different cell line produces a desired growth factor which becomes associated with said matrix and remains with said matrix upon removal of the different cell line.

25. The method of claim 24 wherein said different cell line comprises heterologous gene sequences for causing the production of the growth factor desired.

* * * * *